(12) United States Patent
Ao (10) Patent No.: US 11,504,311 B2
(45) Date of Patent: Nov. 22, 2022

(54) BORON NITRIDE NANOMATERIAL COMPOSITIONS (71) Applicant: Cleveland State University, Cleveland, OH (US)

(72) Inventor: Geyou Ao, Westlake, OH (US)

(73) Assignee: CLEVELAND STATE UNIVERSITY, Cleveland, OH (US)

(*) Notice: Subject to any disclaimer, the term of this patent is extended or adjusted under 35 U.S.C. 154(b) by 11 days.

(21) Appl. No.: 17/249,619

(22) Filed: Mar. 8, 2021

(65) Prior Publication Data
US 2021/0275412 A1 Sep. 9, 2021

Related U.S. Application Data (60) Provisional application No. 62/985,916, filed on Mar. 6, 2020.

(51) Int. Cl.
A61K 8/19 (2006.01)
B01F 3/08 (2006.01)
C01B 21/064 (2006.01)
A61K 8/06 (2006.01)
A61K 8/73 (2006.01)
A61K 8/66 (2006.01)
A61K 8/60 (2006.01)
A61Q 17/04 (2006.01)
B01F 23/411 (2022.01)
B82Y 40/00 (2011.01)

(52) U.S. Cl.
CPC ............ A61K 8/19 (2013.01); A61K 8/062 (2013.01); A61K 8/064 (2013.01); A61K 8/606 (2013.01); A61K 8/66 (2013.01); A61K 8/73 (2013.01); A61Q 17/04 (2013.01); B01F 23/4111 (2022.01); C01B 21/064 (2013.01); A61K 2800/413 (2013.01); A61K 2800/622 (2013.01); A61K 2800/82 (2013.01); B82Y 40/00 (2013.01); C01P 2004/13 (2013.01); C01P 2004/22 (2013.01); C01P 2004/24 (2013.01); C01P 2004/64 (2013.01)

(58) Field of Classification Search
None
See application file for complete search history.

(56) References Cited

U.S. PATENT DOCUMENTS

2007/0280895 A1* 12/2007 Weimer .................. A61K 8/29
424/59

OTHER PUBLICATIONS

Smith, Michael W et al., "Very long single- and few-walled boron nitride nanotubes via the pressurized vapor/condenser method", Nanotechnology 20 (2009), Nov. 12, 2009, 6 pages.

Fathalizadeh, Aidin et al., "Scaled Synthesis of Boron Nitride Nanotubes, Nanoribbons, and Nanococoons Using Direct Feedstock Injection into an Extended-Pressure, Inductively-Coupled Thermal Plasma", Nona Lett. 2014, 14, pp. 4881-4886.

Kim, Keun Su et al., "Hydrogen-Catalyzed, Pilot-Scale Production of Small-Diameter Boron Nitride Nanotubes and Their Macroscopic Assemblies", American Chemical Society, vol. 8, No. 6, pp. 6211-6220, 2014.

(Continued)

Primary Examiner — Dominic Lazaro
(74) Attorney, Agent, or Firm — Fay Sharpe LLP (57) ABSTRACT Compositions contain boron nitride nanomaterials at least partially coated with biomolecules.

20 Claims, 11 Drawing Sheets (56) References Cited

OTHER PUBLICATIONS

Adnan, Mohammed et al., "Extraction of Boron Nitride Nanotubes and Fabrication of Macroscopic Articles Using Chlorosulfonic Acid", 2018 American Chemical Society, Nano Lett 2018, 18, 1615-1619.
Kleinerman, Olga et al., "Dissolution and Characterization of Boron Nitride Nanotubes in Superacid", 2017 American Chemical Society, Langmuir 2017, 33, 14340-14346.
Ao, Geyou et al., "Cholesteric and Nematic Liquid Crystalline Phase Behavior of Double-Stranded DNA Stabilized Single-Walled Carbon Nanotube Dispersions", 2011 American Chemical Society, vol. 5, No. 2, 1450-1458, 2011.

* cited by examiner

BORON NITRIDE NANOMATERIAL COMPOSITIONS

This application claims priority to U.S. Provisional Application Ser. No. 62/985,916, filed Mar. 6, 2020, which is incorporated by reference herein in its entirety.

BACKGROUND

The present disclosure relates to stabilized compositions containing boron nitride nanomaterials.

Traditionally, micron-size $TiO_2$ as UVB 290-320 nm filter and ZnO as UVA 320-400 nm filters were used in sunscreen products. In addition, nanoparticles of $TiO_2$ and ZnO with size less than 100 nm were introduced to overcome the drawback of opaque and white streak appearance of sunscreen formulated with micron size particles, as well as modulating the UV absorption range. However, these inorganic nanoparticles are photoreactive and prone to oxidation, leading to their cyto- and geno-toxic concerns with long-term exposure to skin. These concerns cannot be completely prevented by the coating of the nanoparticles.

It would be desirable to develop new compositions that overcome the aforementioned deficiencies.

BRIEF DESCRIPTION

Disclosed, in some embodiments, is an emulsion containing: a solvent; an oil; and a boron nitride nanomaterial at least partially coated with a biocompatible material.

In some embodiments, the solvent and coated boron nitride nanomaterial define a dispersed phase; and the oil defines a continuous phase.

The boron nitride nanomaterial may be a hexagonal boron nitride nanosheet.

In some embodiments, the biocompatible material is a biopolymer.

The biocompatible material may be DNA and polysaccharides, such as pectin.

In some embodiments, the biocompatible material is at least one protein.

The protein may be selected from the group consisting of lysozyme and bovine serum albumin.

In some embodiments, the biocompatible material is a non-ionic surfactant.

The non-ionic surfactant may be polyethylene glycol sorbitan monooleate.

In some embodiments, the solvent contains water, optionally in combination with dimethyl sulfoxide (DMSO) or at least one alcohol.

The alcohol may be selected from methanol (MeOH), ethanol (EtOH), and isopropyl alcohol (IPA).

Products comprising the emulsion are also disclosed.

Disclosed, in other embodiments, is a composition containing: a hexagonal boron nitride nanosheet at least partially coated with a biocompatible material; and a solvent. It should be understood that reference to a composition containing "a hexagonal boron nitride nanosheet" does not preclude the composition from containing a plurality of such nanosheets.

Products comprising the composition are also disclosed.

Disclosed, in additional embodiments, are boron nitride nanomaterial compositions containing a boron nitride nanomaterial at least partially coated with a biocompatible material.

Disclosed, in further embodiments, is a process for forming an emulsion comprising: adding a boron nitride nanomaterial composition (e.g., a dispersion containing boron nitride coated with biopolymer) to a mixture comprising oil and water; and mixing the mixture with the boron nitride nanomaterial.

The mixing may include mild bath sonication.

In some embodiments, the emulsion is a water-in-oil emulsion. In other embodiments, the emulsion is an oil-in-water emulsion.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

The present disclosure may be understood more readily by reference to the following detailed description of desired embodiments included therein and the drawings. In the following specification and the claims which follow, reference will be made to a number of terms which shall be defined to have the following meanings.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent can be used in practice or testing of the present disclosure. All publications, patent applications, patents, and other references mentioned herein are incorporated by reference in their entirety. The materials, methods, and articles disclosed herein are illustrative only and not intended to be limiting.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases that require the presence of the named ingredients/steps and permit the presence of other ingredients/steps. However, such description should be construed as also describing compositions, mixtures, or processes as "consisting of" and "consisting essentially of" the enumerated ingredients/steps, which allows the presence of only the named ingredients/steps, along with any impurities that might result therefrom, and excludes other ingredients/steps.

Unless indicated to the contrary, the numerical values in the specification should be understood to include numerical values which are the same when reduced to the same number of significant figures and numerical values which differ from the stated value by less than the experimental error of the conventional measurement technique of the type used to determine the particular value.

All ranges disclosed herein are inclusive of the recited endpoint and independently combinable (for example, the range of "from 2 to 10" is inclusive of the endpoints, 2 and 10, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The present disclosure relates in part to the development of applications of boron nitride nanomaterials in new multifunctional, broad spectrum (290-400 nm) sunscreen products including emulsions, creams, lotions, sprays, and powders. In contrast to $TiO_2$ and ZnO nanoparticles, hexagonal boron nitride nanosheets are thermally and chemically inert and stable against oxidation, have lateral size on the micron scale, and absorb UV light. The high oil absorption and lubricity of hexagonal boron nitride provide smooth coverage on skin. The 2D plate-like structure of hexagonal boron nitride also provides high mass potency and great interfacial activity at the liquid-liquid interfaces. Therefore, stabilization of emulsions can be achieved at reduced material costs. The surface functionality of hexagonal boron nitride can be further tuned by disposing various dispersant molecules on its surface to render improved biocompatibility.

In addition, the superior mechanical strength of boron nitride nanomaterials offers potential applications in strong, protective coatings against UV and neutron radiation, essential for aerospace applications.

The current price for cosmetic grade hexagonal boron nitride is ~$70 per kilogram, significantly less expensive than high purity boron nitride nanotubes (~$100,000 per kilogram for quantity more than a kilogram).

Exfoliated hexagonal boron nitride may be used as an effective stabilizer of emulsions due to the fact that most (e.g., all) atoms reside on the surface of the nanomaterial, therefore, most (e.g., every) atoms participate directly in stabilization at the liquid-liquid interface.

Figure 1:
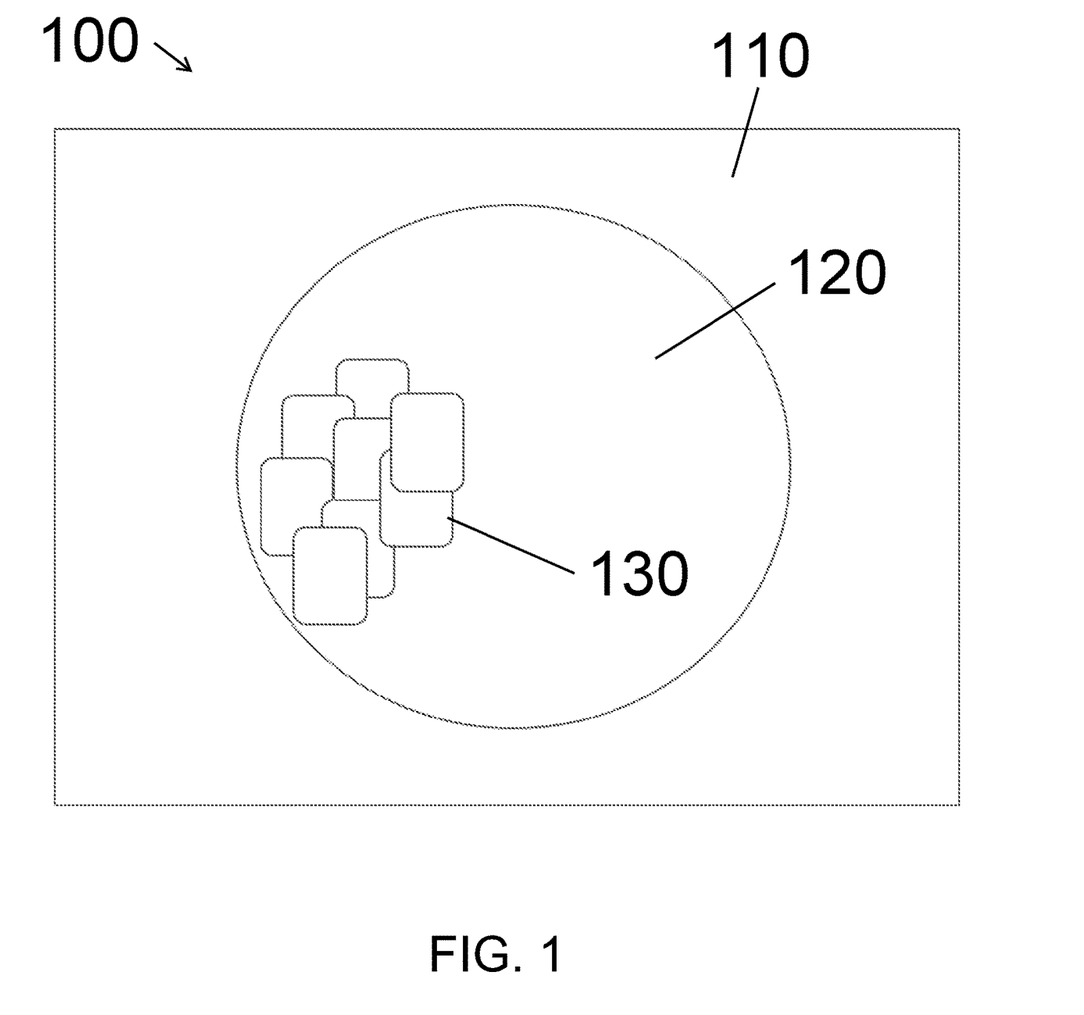
FIG. 1 is a schematic illustration of a water-in-oil type emulsion stabilized by surface engineered hexagonal boron nitride nanosheets (hBN). The surface hydrophobicity and hydrophilicity of hBN nanosheets coated by biomolecules allows the control of the emulsion type such as water-in-oil and oil-in-water emulsions.

FIG. 1 schematically illustrates a water-in-oil type emulsion 100 stabilized by surface engineered hexagonal boron nitride. The oil 110, water 120, and hexagonal boron nitride 130 are labeled.

Surface engineering the hexagonal boron nitride by introducing functional groups through covalent and noncovalent chemistry will further provide emulsions of tunable properties.

The surface engineering may include surface complexing with biocompatible materials.

Non-limiting examples of biocompatible materials includes one or more biomolecules and/or non-ionic surfactants.

The biomolecules may be selected from one or more of DNA, RNA, proteins, polypeptides, and polysaccharides. Non-limiting examples of proteins include lysozyme and bovine serum albumin. Non-limiting examples of polysaccharides include pectin and cellulose.

Non-limiting examples of polysaccharides include alginate, high M-content alginates, polymannuronic acid, polymannuronates, hyaluronic acid, chitosan, chitin, cellulose, starch, glycogen, guar gum, locust bean gum, dextran, levan, inulin, cyclodextran, agarose, xanthan gum, carageenan, heparin, pectin, gellan gum, and scleroglucan.

Polycations such as polyamino acids are also contemplated. Non-limiting examples of polyamino acids include polyhistidine, polylysine, polyornithine, polyarginine, polyalanine-polylysine, poly(histidine, glutamic acid)-polyalanine-polylysine, poly(phenylalanine, glutamic acid)-polyalanine-polylysine, poly(tyrosine, glutamic acid)-polyalanine-polylysine, collagen, and gelatin.

Lipids are also contemplated. Non-limiting examples of lipids include phosphatidylethanolamine, phosphatidylserine, phosphatidylinositol, phosphatidylglycerol, dilaurylphosphatidic acid, and dipalmitoyl phosphatidyl glycerol.

Non-limiting examples of nonionic surfactants include those derived from polyethoxylated sorbitan and oleic acid, such as polyethylene glycol sorbitan monooleate which is also known as TWEEN® 80.

The compositions of the present disclosure may be used in UV protective coatings and cosmetic products with UV protection. Non-limiting examples include sunscreen emulsions, creams, lotions, sprays, and powders.

In other embodiments, the compositions may be used in semiconductor applications. Non-limiting examples include insulating thermal management packages of electronic devices and thermal interface materials (TIM).

Advantageously, stable dispersions of hexagonal boron nitride at a broad concentration range in various solvents provide tunability in formulations and assist liquid phase processing of products widely used in industry. For sunscreen formulations, the effectiveness of hBN as an emulsion stabilizer is targeted at low concentrations (<2 mass %, preferably <1 mass %). In some embodiments, the minimum concentration is about 0.5 mass %.

Non-limiting examples of solvents include water and/or one or more alcohols. In some embodiments, the alcohol is selected from ethanol, methanol, isopropyl alcohol, and a mixture of any combination of two or more thereof.

Non-limiting examples of mass ranges for the boron nitride nanomaterial include about 0.001 mass % to about 12 mass %, about 0.01 mass % to about 5 mass %, about 0.1 mass % to about 2 mass %, and about 0.5 mass % to about 1 mass %. These ranges are merely examples and it is contemplated that values and limits from different ranges may be combined together to define additional ranges that are considered to be at least implicitly disclosed herein.

As a dispersant, biopolymers (such as DNA and pectin) enable uniform dispersions of single- and few-layers of hexagonal boron nitride nanosheets in solvents at high concentrations (e.g., up to ~12 mass %), and exfoliated DNA-hexagonal boron nitride nanosheets that are individually dispersed and not associated provides enhanced biocompatibility and high mass potency needed for producing emulsified products at lower material costs. The nanosheets may contain from 1 to about 11 layers, including 1 to about 5 layers, and 1 to about 3 layers. Nanosheets containing 1, 2, 3, 4, 5, 6, 7, 8, 9, 10, and 11 layers are expressly contemplated.

The biopolymer (e.g., DNA) disposed on the surface of hexagonal boron nitride nanosheets makes robust DNA-hexagonal boron nitride hybrids that can be easily re-suspended in water, alcohol/water mixtures, and DMSO/water mixtures after multiple processing such as precipitation and membrane filtration.

The compositions enable the production of final products with multifunctional properties including at least one of improved broad-spectrum UV protection, photostability, chemical stability, cooling effect, moisture retention, oil control, and smooth coverage that are not found in other existing materials.

A process for producing stable aqueous dispersions of 1D nanostructures of boron nitride nanotubes by DNA at boron nitride nanotube concentrations of as high as mass % and assembly of solid aligned boron nitride nanotube films is disclosed in U.S. patent application Ser. No. 16/775,319, filed Jan. 29, 2020 and which is incorporated by reference herein in its entirety. Methods for making uniform dispersions of boron nitride (BN) nanomaterials (boron nitride nanotubes and hexagonal boron nitride) that are surface complexed with biomolecules (DNA, lysozyme, pectin) in water, alcohol/water mixtures, and DMSO/water mixtures are described. The use of alcohol/water mixtures and DNA allow uniform dispersions of BN nanomaterials with mild bath sonication. This provides the advantage of maintaining the size of synthetic material during processing, as nanomaterial size is one of the key factors determining properties of the final products such as aligned films and fibers and emulsions. High purity, crystalline synthetic hexagonal boron nitride with an average lateral size of 10-12 μm may be used. Stable liquid dispersions of BN nanomaterials enable their scalable manufacturing using existing liquid phase processing techniques utilized for many commercial products, such as coatings, fiber spinning, and emulsions.

The dispersion method developed for boron nitride nanotubes is directly applicable for exfoliating 2D allotrope of boron nitride nanomaterials, hexagonal boron nitride to single- and few-layered nanosheets, in various solvents including water, alcohol/water mixtures, and DMSO/water mixtures. Stable dispersions of hexagonal boron nitride surface coated by DNA (DNA-hexagonal boron nitride) render biocompatibility, dispersion stability at a broad concentration of hexagonal boron nitride, and compatibility in liquid phase processing of many cosmetic applications such as sunscreen product formulations. The multifunctionality of hexagonal boron nitride nanosheets will enable it to serve as both an effective stabilizer of emulsions and a UV filter as well as providing added values for the final product including improved anti-oxidation, cooling effect, sunscreen photostability, and smooth coverage.

The dispersion may be formed by mixing the boron nitride nanomaterial and biocompatible material in a solvent. The emulsion may be formed by combining the dispersion with an oil. Optionally, the dispersion may be purified before forming the emulsion. Alternatively, the emulsion may be formed without a previous dispersion formation by mixing the boron nitride nanomaterial, the biocompatible material, the solvent, and the oil.

A mass ratio of the boron nitride nanomaterial to the biocompatible material may be in the range of about 1:1 to about 1:10 (e.g., about 1:2) or about 1:1 to about 2:1.

The dispersion may be formed in a mixer. In some embodiments, the dispersion is formed via sonication (e.g., ultra-sonication). Sonication involves applying sound energy to agitate particles. Ultrasonication is sonication wherein the sound waves have a frequency exceeding the upper audible limit of human hearing. In some embodiments, the sound waves have a frequency of at least 20 kHz.

In other embodiments, the sonication is a mild bath sonication (e.g., using a Fisher Scientific, Ultrasonic Bath 5.7 L).

Sonication may be performed for a time period in the range of about 0.1 to about 50 hours, including from about 0.5 to about 40 hours, from about 1 to about 30 hours, and from about 6 to about 24 hours.

When the biocompatible material is DNA, the DNA may be single-stranded DNA or double-stranded DNA. In some embodiments, the single stranded DNA is represented by the following formula: $(GT)_n$, wherein n is the number of repeated units. n may be in the range of from about 2 to about 100, including from about 3 to about 40.

In other embodiments, the biocompatible material is RNA.

The following examples are provided to illustrate the devices and methods of the present disclosure. The examples are merely illustrative and are not intended to limit the disclosure to the materials, conditions, or process parameters set forth therein.

EXAMPLES

Dispersions of Synthetic Boron Nitride Nanotubes Using DNA as a Dispersant in Alcohol/Water Mixtures Dispersions of synthetic boron nitride nanotubes by DNA (deoxyribonucleic acid from herring sperm, <50 bp, denatured, Sigma-Aldrich) are prepared in various alcohol/water mixtures with different alcohol contents by mild bath sonication followed by a centrifugation to extract a majority of individually dispersed nanotubes by removing larger bundles of nanotubes and impurities. The resulting DNA-wrapped boron nitride nanotube hybrids in supernatant dispersions yield longer nanotubes (average length 372±177 nm) compared to that of previously reported DNA-boron nitride nanotube dispersions (average length 268 ±110 nm) by tip sonication in water. In addition, DNA-boron nitride nanotubes hybrids obtained in alcohol/water mixtures are stable under various processing including precipitation, membrane filtration, and washing for purification and exchanging solvents between water and alcohol/water mixtures. A bath sonication of re-suspended nanotubes with additional DNA is recommended for long-term storage of purified nanotube dispersions. A mild bath sonication provides a lower ultrasonic power input of approximately 20 W/L (<100 W/L, <50 W/L, <40 W/L, <30 W/L), which is about 1000 times lower than that of a typical probe tip sonication. The sonication energy for an ultrasonic bath is low and distributes over a large volume of liquid medium in the tank.

Figure 2:
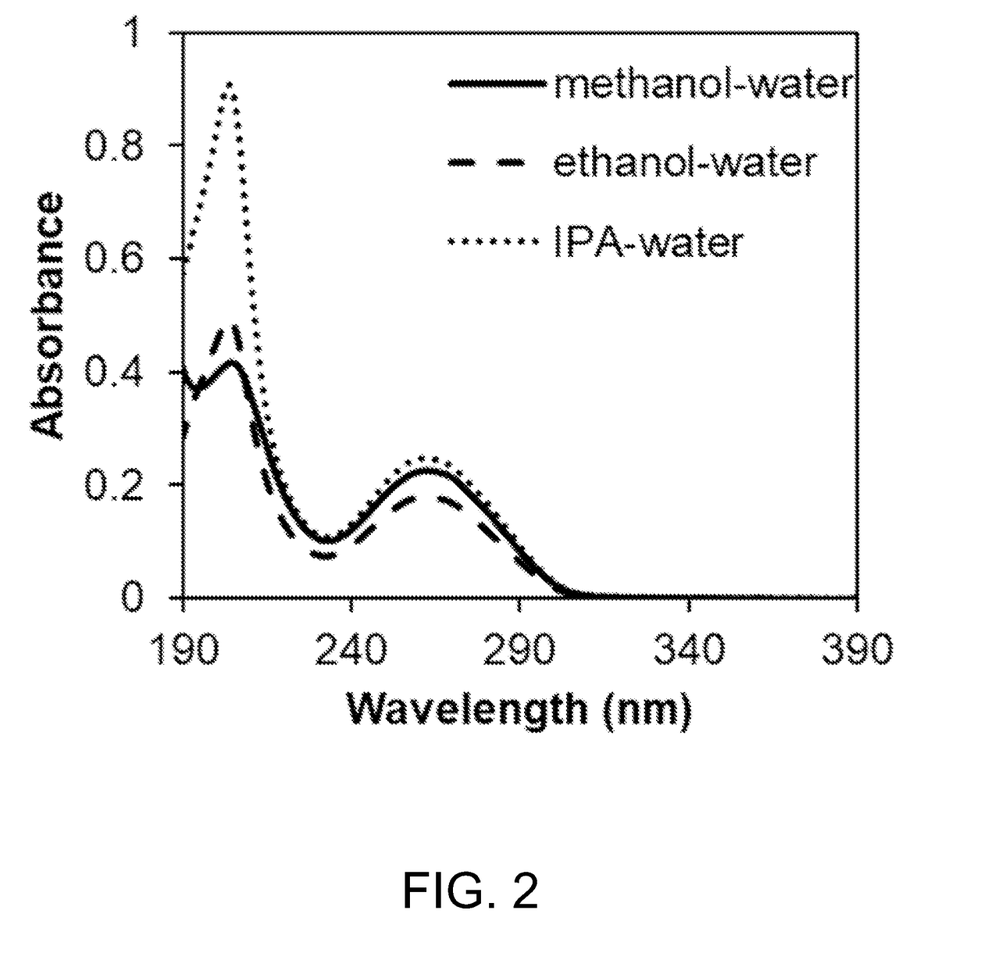
FIG. 2 is a graph of absorbance spectra of supernatant dispersions (i.e., samples collected after centrifuging sonicated dispersions of boron nitride nanomaterial) of 1 mg/mL boron nitride nanotubes in 1 mg/mL DNA in different alcohol and water mixtures of 1:1 volume ratio. Samples were diluted by a factor of 100× in deionized water for UV-vis absorbance measurements.

FIG. 2 is a graph of absorbance spectra of supernatant dispersions of 1 mg/mL boron nitride nanotubes in 1 mg/mL DNA in alcohol and water mixtures of 1:1 volume ratio. Alcohols used include methanol (MeOH), ethanol (EtOH), and isopropyl alcohol (IPA).

Figure 3:
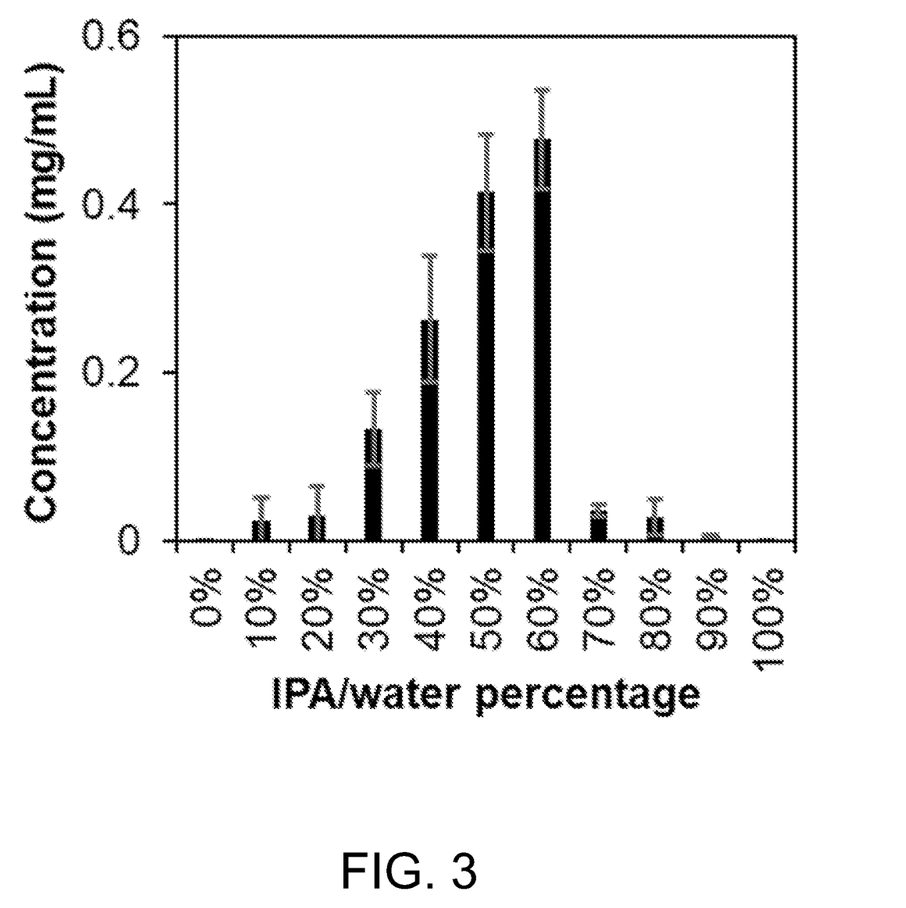
FIG. 3 is a bar graph comparing the concentration of boron nitride nanotubes remaining in supernatant dispersions of 1 mg/mL DNA-1 mg/mL boron nitride nanotubes in IPA/water mixtures with varying alcohol contents.

FIG. 3 is a graph comparing the concentration of boron nitride nanotubes remaining in supernatant dispersions of 1 mg/mL DNA-1 mg/mL boron nitride nanotubes in IPA/water mixtures with varying alcohol contents.

An absorption peak at 205 nm wavelength corresponds to that of boron nitride nanotubes (FIG. 3). Concentration of boron nitride nanotubes can be determined using the extinction coefficient of 0.0926 L mg$^{-1}$ cm$^{-1}$ at 205 nm. It showed that up to 60 vol % IPA, the dispersion yield of boron nitride nanotubes in IPA/water mixtures increased with increasing alcohol contents and a dispersion yield of approximately 47% was obtained in a IPA/water mixture with 60 vol % IPA (FIG. 3).

Figure 4:
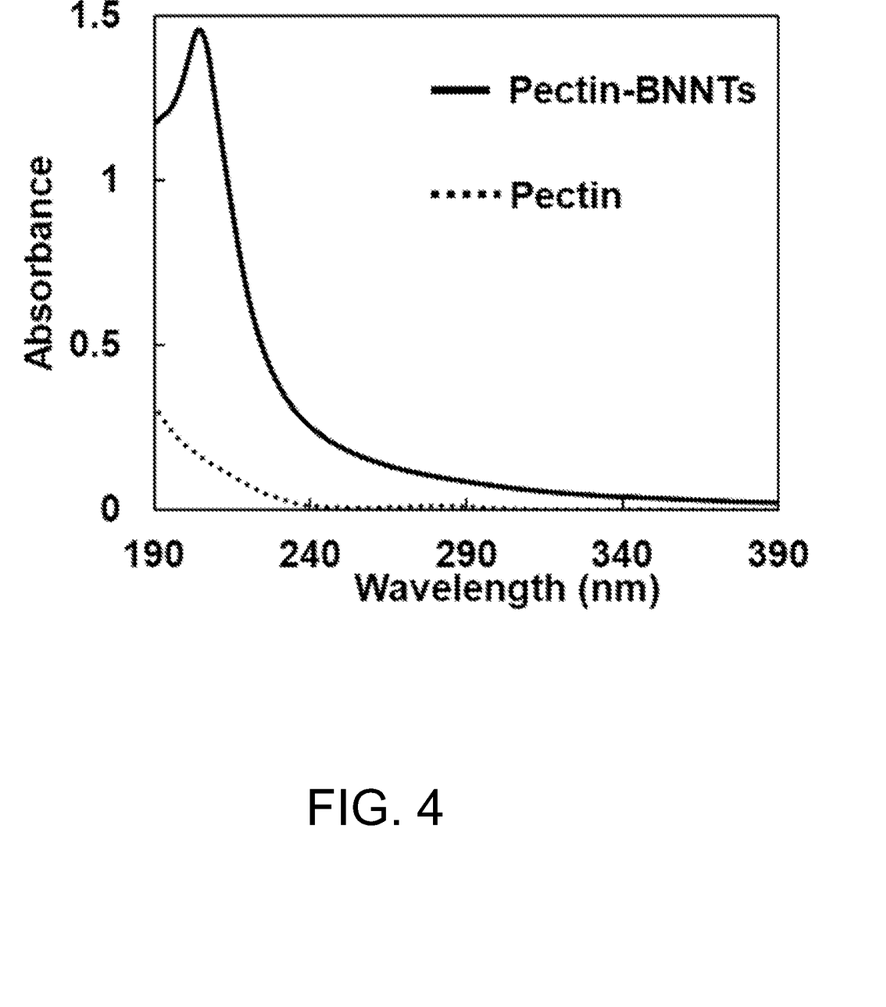
FIG. 4 is a graph of absorbance spectra of supernatant dispersions of 1 mg/mL boron nitride nanotubes in 1 mg/mL pectin in water and 1 mg/mL pectin only in water. Samples were diluted by a factor of 75× in deionized water for UV-vis absorbance measurements.

Dispersions of Synthetic Boron Nitride Nanotubes Using Pectin as a Dispersant in Water FIG. 4 is a graph of absorbance spectra of supernatant dispersions of 1 mg/mL boron nitride nanotubes in 1 mg/mL pectin in water and 1 mg/mL pectin only in water.

Figure 5:
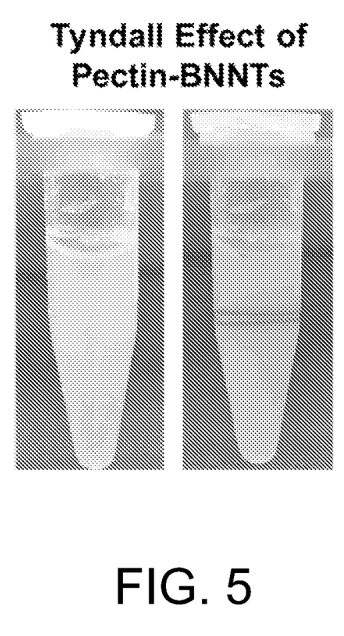
FIG. 5 includes photographs of supernatant dispersions of 1 mg/mL boron nitride nanotubes in 1 mg/mL pectin in water and the observed Tyndall effect (distinct light scattering by suspended colloids) where the path of the (red) laser beam is clearly distinguishable in the sample.

FIG. 5 includes photographs of supernatant dispersions of 1 mg/mL boron nitride nanotubes in 1 mg/mL pectin in water and the observed Tyndall effect (distinct light scattering by suspended colloids) where the path of the (red) laser beam is clearly distinguishable in the sample.

Dispersions of Hexagonal Boron Nitride Nanosheets Using DNA as a Dispersant in Alcohol/Water Mixtures and Emulsion Stabilization The dispersion method developed for boron nitride nanotubes is directly applicable for exfoliating 2D hexagonal boron nitride to single- and few-layered nanosheets, in various solvents including water and alcohol/water mixtures. The resulting DNA-coated hexagonal boron nitride nanosheets are stable after membrane filtration and washing for exchanging solvents between water and alcohol/water mixtures.

Figure 6:
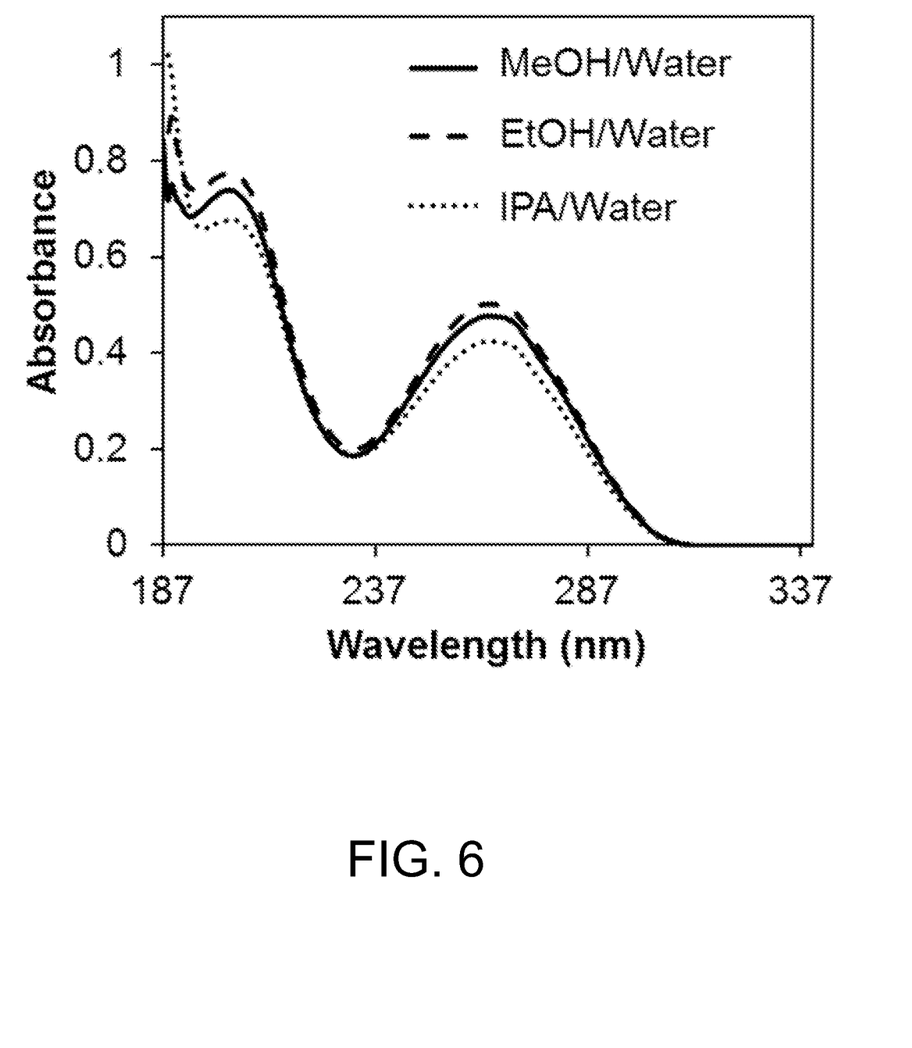
FIG. 6 is a graph of absorbance spectra of supernatant dispersions of 1 mg/mL hexagonal boron nitride in 1 mg/mL DNA in different alcohol and water mixtures of 1:1 volume ratio. Samples were diluted by a factor of 100× in deionized water for UV-vis absorbance measurements.

FIG. 6 is a graph of absorbance spectra of supernatant dispersions of 1 mg/mL hexagonal boron nitride in 1 mg/mL DNA in alcohol and water mixtures of 1:1 volume ratio. Alcohols used include methanol (MeOH), ethanol (EtOH), and isopropyl alcohol (IPA).

Figure 7:
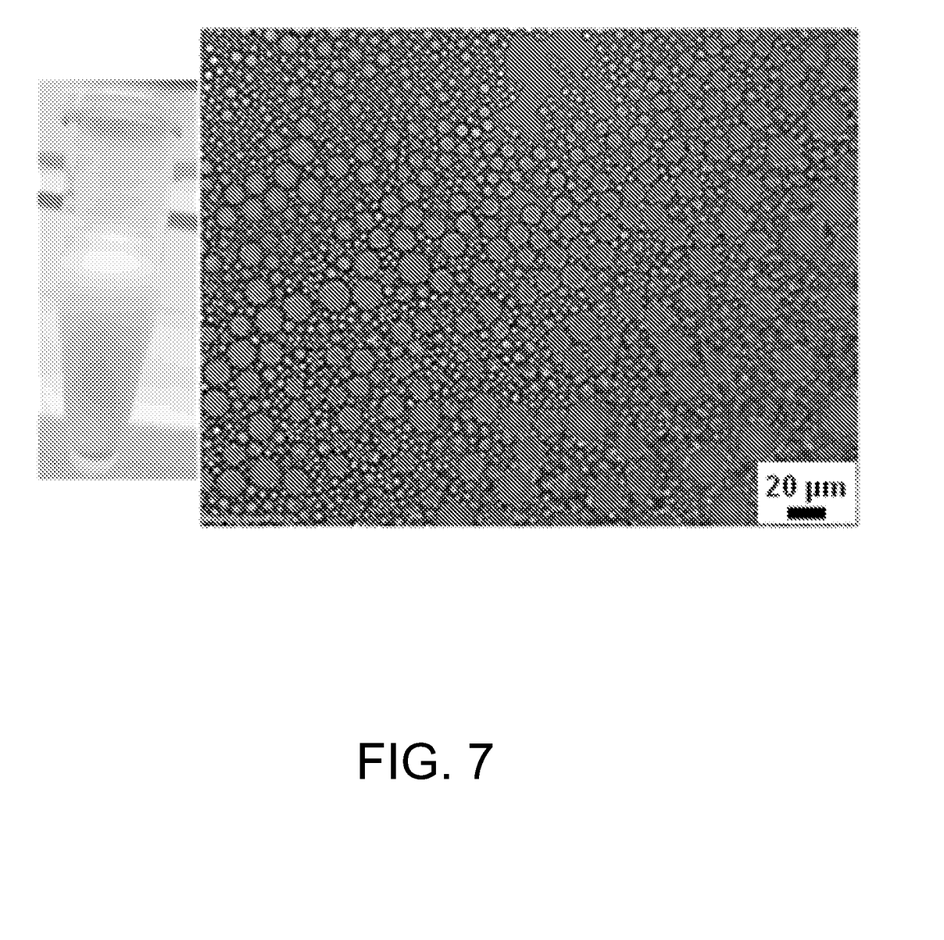
FIG. 7 includes a photograph of a hexagonal boron nitride (~0.1 mass %) stabilized oil/water emulsion with oil:water volume ratio of 1:1 and a corresponding micrograph.

FIG. 7 is a photograph of hexagonal boron nitride stabilized oil/water emulsion with oil:water volume ratio of 1:1 and its corresponding optical microscopy image. The hexagonal boron nitride concentration of the emulsion is ~0.1 mass %.

Exfoliated hexagonal boron nitride has an absorption peak near 205 nm wavelength. The broad peak near 270 nm corresponds to excess unbound DNA (FIG. 6). The exfoliated hexagonal boron nitride was then used to stabilize oil (N7.5, hydrocarbon oil, Cannon Instrument Company)-water emulsion at neutral pH using ~0.1 mass % hexagonal boron nitride (FIG. 7). Typically, an appropriate amount of exfoliated hBN nanosheets dispersions were added to oil and water mixtures and the emulsion was prepared by a tip sonication at 8 W power for 5 min. Parameters including the concentration, size, and surface functionality of hexagonal boron nitride, the type of oil, and the oil/water ratio will affect the stability and properties of resulting emulsions such as the size of stabilized liquid droplets and the type of emulsions formed.

Additional Examples

Figure 8:
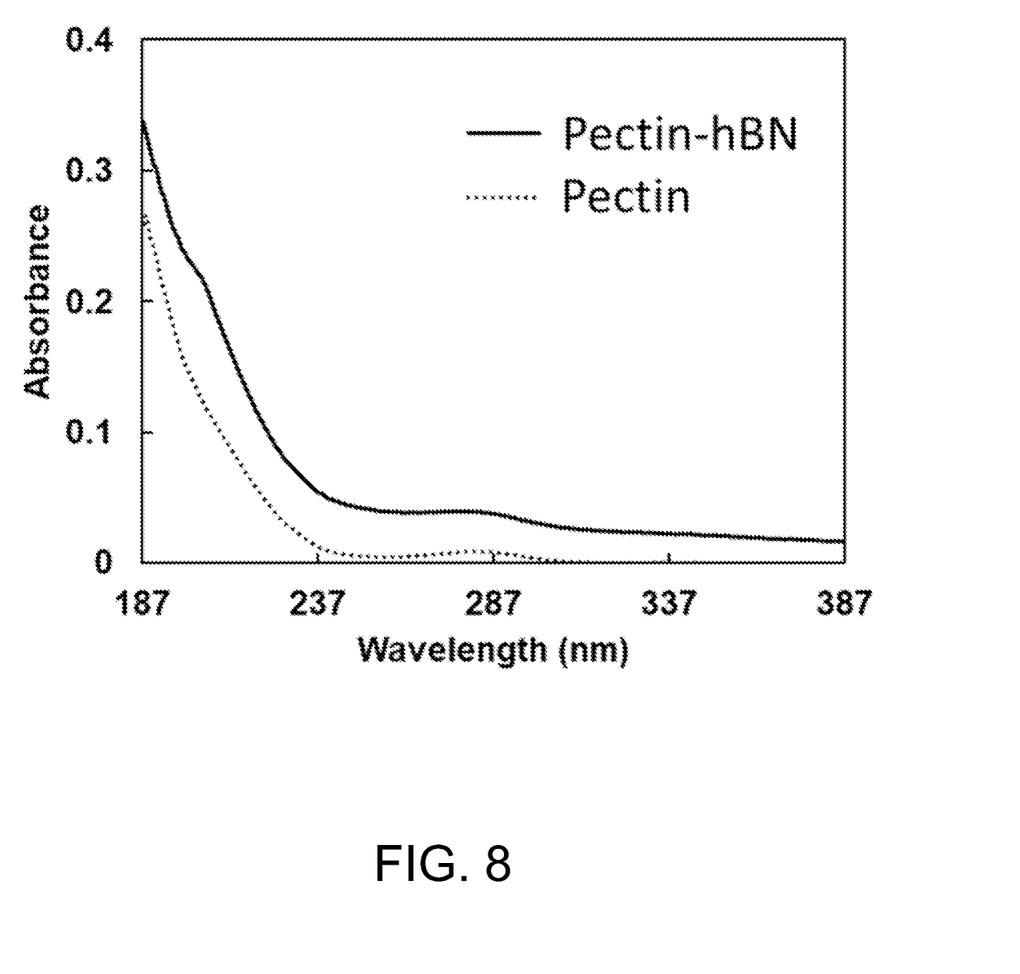
FIG. 8 is a graph of absorbance spectra of bulk dispersions (i.e., samples collected directly after sonication of boron nitride nanomaterials without centrifugation) of 1 mg/mL hexagonal boron nitride in 4 mg/mL pectin in water and 4 mg/mL pectin only in water. Samples were diluted by a factor of 100× in deionized water for UV-vis absorbance measurements.

FIG. 8 is a graph of absorbance spectra of bulk dispersions (i.e., samples collected directly after sonication of boron nitride nanomaterials without centrifugation) of 1 mg/mL hexagonal boron nitride in 4 mg/mL pectin in water and 4 mg/mL pectin only in water.

Figure 9:
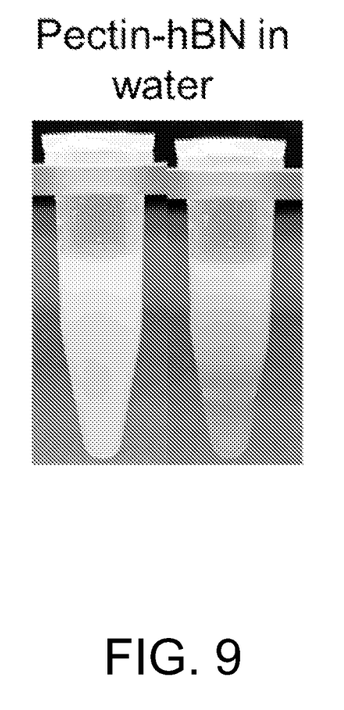
FIG. 9 includes photographs of bulk dispersions of 1 mg/mL hexagonal boron nitride in 4 mg/mL pectin in water and the observed Tyndall effect of dispersions.

FIG. 9 includes photographs of bulk dispersions of 1 mg/mL hexagonal boron nitride in 4 mg/mL pectin in water and the observed Tyndall effect of dispersions.

Figure 10:
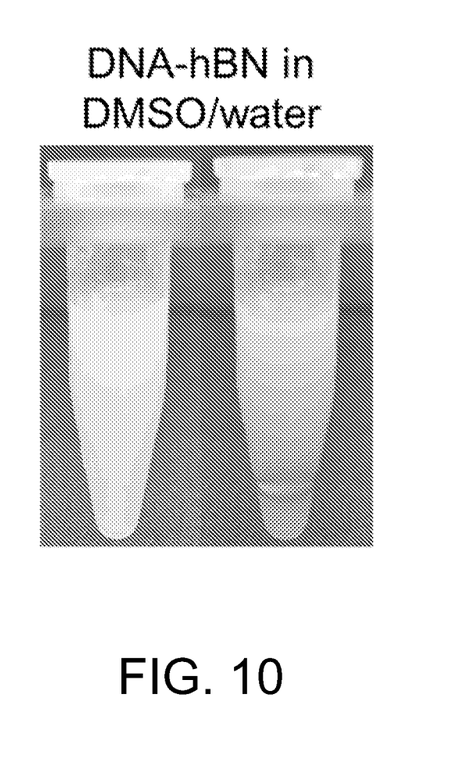
FIG. 10 includes photographs of bulk dispersions of 1 mg/mL hexagonal boron nitride in 2 mg/mL pectin in water and dimethyl sulfoxide (DMSO) mixture of 1:1 volume ratio.

FIG. 10 includes photographs of bulk dispersions of 1 mg/mL hexagonal boron nitride in 2 mg/mL pectin in water and dimethyl sulfoxide (DMSO) mixture of 1:1 volume ratio.

Figure 11:
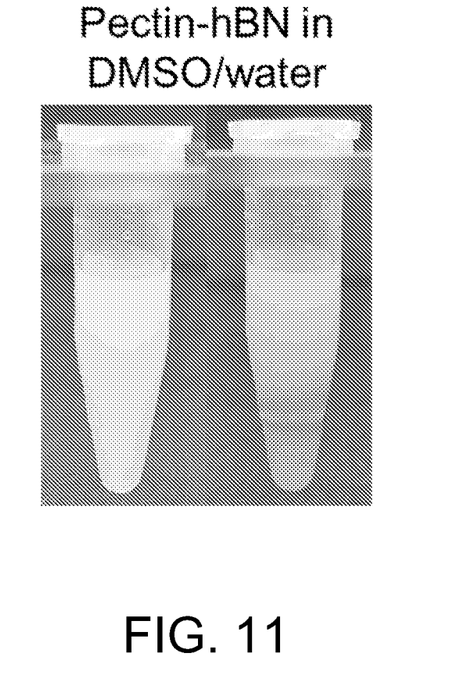
FIG. 11 includes photographs of bulk dispersions of 1 mg/mL hexagonal boron nitride in 2 mg/mL DNA in water and dimethyl sulfoxide (DMSO) mixture of 1:1 volume ratio.

FIG. 11 includes photographs of bulk dispersions of 1 mg/mL hexagonal boron nitride in 2 mg/mL DNA in water and dimethyl sulfoxide (DMSO) mixture of 1:1 volume ratio.

This written description uses examples to describe the disclosure, including the best mode, and also to enable any person skilled in the art to make and use the disclosure. Other examples that occur to those skilled in the art are intended to be within the scope of the present disclosure if they have structural elements that do not differ from the same concept, or if they include equivalent structural elements with insubstantial differences. It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. An emulsion comprising:
   a solvent;
   an oil; and
   a boron nitride nanomaterial at least partially coated with a biocompatible material.

2. The emulsion of claim 1, wherein the solvent and coated boron nitride nanomaterial define a dispersed phase; and wherein the oil defines a continuous phase.

3. The emulsion of claim 1, wherein the boron nitride nanomaterial comprises a hexagonal boron nitride nanosheet.

4. The emulsion of claim 1, wherein the nanomaterial has a thickness of less than or equal to about 5 nm.

5. The emulsion of claim 1, wherein the biocompatible material comprises a biopolymer.

6. The emulsion of claim 1, wherein the biocompatible material comprises DNA.

7. The emulsion of claim 1, wherein the biocompatible material comprises a polysaccharide.

8. The emulsion of claim 7, wherein the polysaccharide is pectin.

9. The emulsion of claim 1, wherein the biocompatible material comprises a protein.

10. The emulsion of claim 9, wherein the protein is selected from the group consisting of lysozyme and bovine serum albumin.

11. The emulsion of claim 1, wherein the biocompatible material comprises a non-ionic surfactant.

12. The emulsion of claim 11, wherein the non-ionic surfactant is polyethylene glycol sorbitan monooleate.

13. The emulsion of claim 1, wherein the solvent is selected from the group consisting of water and dimethyl sulfoxide.

14. The emulsion of claim 1, wherein the solvent comprises water and at least one alcohol.

15. The emulsion of claim 14, wherein the at least one alcohol is selected from the group consisting of methanol, ethanol, and isopropyl alcohol.

16. A composition comprising:
    a hexagonal boron nitride nanosheet at least partially coated with a biocompatible material; and
    a solvent.

17. The composition of claim 16, wherein the biocompatible material is selected from the group consisting of a biopolymer, a polysaccharide, and a protein.

18. A process for forming the emulsion of claim 1, the process comprising:
    adding the boron nitride nanomaterial to a mixture comprising the oil and the solvent; and
    mixing the mixture with the boron nitride nanomaterial.

19. The process of claim 18, wherein the mixing comprises mild bath sonication.

20. The process of claim 18, wherein the emulsion is a water-in-oil emulsion or an oil-in-water emulsion.

* * * * *